United States Patent
Lezdey et al.

(10) Patent No.: US 6,379,684 B1
(45) Date of Patent: Apr. 30, 2002

(54) COSMETIC COMPOSITIONS CONTAINING CROMOLYN COMPOUNDS FOR REVITALIZING THE SKIN

(75) Inventors: John Lezdey, Indian Rocks Beach; K. Anne Kronis, Tampa; Darren Lezdey, Indian Rocks Beach, all of FL (US)

(73) Assignee: Alphamed Pharaceutical Corp., Clearwater, FL (US)

( * ) Notice: Subject to any disclaimer, the term of this patent is extended or adjusted under 35 U.S.C. 154(b) by 0 days.

(21) Appl. No.: 09/846,584

(22) Filed: May 2, 2001

(51) Int. Cl.$^7$ .................. A61K 7/00; A61K 38/16; A61K 31/665; A01N 37/18
(52) U.S. Cl. ............... 424/401; 514/2; 514/8; 514/12; 514/21; 514/100; 514/844; 514/937; 514/944
(58) Field of Search ................ 424/401; 514/844, 514/937, 944, 100, 2, 8, 12, 21

(56) References Cited

U.S. PATENT DOCUMENTS

| | | | | |
|---|---|---|---|---|
| 5,190,917 A | * | 3/1993 | Lezdey et al. | 514/12 |
| 5,290,762 A | * | 3/1994 | Lezdey et al. | 514/8 |
| 5,326,790 A | * | 7/1994 | Thornfeldt | 514/784 |
| 5,532,270 A | * | 7/1996 | Clemente et al. | 514/456 |
| 5,686,489 A | * | 11/1997 | Yu et al. | 514/557 |
| 6,096,327 A | * | 8/2000 | Lezdey et al. | 424/401 |

* cited by examiner

Primary Examiner—Jose' G. Dees
Assistant Examiner—Marina Lamm
(74) Attorney, Agent, or Firm—John Lezdey

(57) ABSTRACT

Cosmetic compositions and methods are provided for revitalizing the skin especially where it is placed in an environment that can cause injury to the skin. The compositions contain an effective amount of cromolyn compounds to provide a prophylactic or repairing effect.

7 Claims, No Drawings

COSMETIC COMPOSITIONS CONTAINING CROMOLYN COMPOUNDS FOR REVITALIZING THE SKIN

FIELD OF THE INVENTION

The present invention relates to cosmetic compositions containing cromolyn compounds. More particularly, there is provided cosmetic compositions containing anti-chymase, anti-tryptase and/or anti-elastase inhibitors, which improves or revitalizes atmosphere damaged skin including chapped lips, wind burn, sun burn and wrinkles resulting therefrom, as well as natural skin eruptions.

BACKGROUND OF THE INVENTION

Human type serine protease inhibitors such as cromolyn compounds have been proposed for use in cosmetic compositions. However, these proteins are expensive and cannot be utilized in many cosmetic preparations since they are subject to degradation by other ingredients and are temperature sensitive with limited shelf-lives.

Cromolyn sodium is commercially available in anti-asthma formulations for its property of preventing mast cell degranulation.

Household pets such as cats and dogs obtain rashes, develop itching as a result of soap, chemicals, insect bites, etc., which are commonly treated with over-the-counter medicaments since they are only minor irritations.

Hydrocortisone has been used with little effect. There is a need for an inexpensive and effective composition for treating pets for their minor irritations, which has a broad spectrum of effects so to be used on undiagnosed causes for the irritation.

SUMMARY OF THE INVENTION

The present invention provides a topical cosmetic composition for improving or revitalizing the texture of skin or as a prophylactic against skin irritations or degradations resulting from exposure to the sun. The composition is especially useful for treating skin damaged by the atmosphere such as sun damaged or wrinkled skin, chapped lips or skin, or to prevent skin eruptions.

The cromolyn compounds, which can be used in the present invention, include cromolyn, cromolyn sodium, disodium cromolyn, the lower alkyl esters and derivatives thereof.

The wound healing properties of cromolyn compounds are helpful in cosmetic preparations, which are intended to cover blemishes or skin eruption.

The compositions of the invention contain at least about 0.5 percent of the cromolyn compounds. The amount of cromolyn compounds, which generally can be used, is about one percent by weight, preferably, about 1 to 10% by weight of composition. Greater amounts can be utilized but are not required to achieve the desired results.

The compositions of the invention can be used in the form of a lotion, creme, gel or solution, depending on the use or treatment contemplated. The extract can be formulated into cosmetic compositions such as lipsticks, hand cremes, after sun compositions, and the like.

Cromolyn compounds possess anti-PAR-2 (protease-activated receptor-2) characteristics so that they affect the inflammatory cascade differently than alpha 1-antitrypsin, which is anti-IgE and anti-glycosylation factors (GEF). It is believed that anti-PAR-2 permits the cromolyn to be effective more quickly on blemishes and rashes, which may not involve mast cells or elevated IgE.

The cromolyn compounds can be used alone or with other skin treatment compounds such as aloe vera.

It is a general object of the invention to provide a cosmetic composition, which contains an effective amount of the cromolyn compound to improve the quality of the skin.

It is another object to provide a cosmetic composition for treating sensitive skins.

It is yet another object to provide a method and topical composition which helps revitalize environmentally damaged skin.

It is a still further object of the invention to provide a method for improving damaged skin as a result of ultra-violet radiation.

It is also an object of the invention to provide a composition having anti-PAR-2 characteristics.

DESCRIPTION OF THE PREFERRED EMBODIMENTS

The present invention provides an improvement in cosmetic compositions by providing safe and natural chymase, tryptase and/or elastase inhibitors which are non-irritating to human or animal skin.

The favorable cosmetic activity of the cromolyn compounds is believed to be the results of the chymase, tryptase and elastase inhibition by the cromolyn compounds before or during inflammation. Also, the control of the elastase permits the laying down of new tissue without degradation resulting from the presence of excess elastase. After a solar peel or removal of the upper dermal layer mechanically or naturally, the new tissue layer which is layed down is more resilient and thereby reduces the wrinkles unless scarring or degradation occurs due to excess elastase. In aging skin, the cromolyn compounds appear to revitalize as well as soften the existing skin. The compositions with the cromolyn compounds have a prophylactic effect and reduce the incidence of skin eruptions or inflammations as a result of the action against serine proteases or mast cell involvement. The compositions are further useful for lightening the skin and to reduce the effect of hyperpigmentation.

The compositions according to the invention may be presented in all forms normally used for topical application, in particular in the form of aqueous, aqueous-alcoholic or, oily solutions, or dispersions of the lotion or serum type, or anhydrous or lipophilic gels, or emulsions of liquid or semi-solid consistency of the milk type, obtained by dispersing a fatty phase in an aqueous phase (O/VV) or vice versa (VV/O), or of suspensions or emulsions of soft, semi-solid consistency of the cream or gel type, or alternatively of microemulsions, of microcapsules, of microparticles or of vesicular dispersions of the ionic and/or nonionic type. These compositions are prepared according to standard methods.

The amounts of the different constituents of the compositions according to the invention are those traditionally used in the cosmetic field.

These compositions constitute, in particular, cleansing, protective, treatment or skin care creams for the face, hands, feet, major anatomical folds or the body (for example day creams, night creams, make-up removal creams, foundation creams, sun-protection creams), fluid foundations, make-up removal milks, protective or skin care body milks, after-sun milks, skin care lotions, gels or foams, such as cleansing or disinfecting lotions, bath compositions, deodorant compositions, aftershave gels or lotions, and compositions for treating certain skin disorders such as those mentioned above.

The sun can produce a series of lesions on the skin, which can be precancerous (e.g. seborrheic, keratoses or actinic keratoses) Treatment with cromolyn compounds reduces the risk of cellular proliferation when applied in a suitable composition after exposure to the sun or ultra-violet radiation.

The compositions according to the intention may also consist of solid preparations constituting cleansing bars or soaps.

The compositions may also be packaged in the form of an aerosol composition containing a propellant agent under pressure.

When the composition of the invention is an emulsion, the proportion of the fatty phase can range from 5% to 80% by weight, and preferably from 5% to 50% by weight, relative to the total weight of the composition. The oils, emulsifiers and coemulisifiers used in the composition in emulsion form are chosen from those traditionally used in the cosmetics. The emulsifier and the coemulsifier are present in the composition in a proportion ranging from 0.3% to 30% by weight, and preferably 0.5 to 30% by weight or, better still, from 0.5 to 20% by weight relative to the total weight of the composition. The emulsion can, in addition, contain lipid vesicles.

When the compositions of the invention is an oily gel or solution, the fatty phase can represent more than 90% of the total weight of the composition.

In a known manner, the composition of the invention may also contain adjuvants which are customary in cosmetics, such as hydrophilic or lipophilic gelling agents, hydrophilic or lipophilic active agents, preservatives, antioxidants, solvents, perfumes, fillers, screening agents, bactericides, odor absorbers and coloring matter. The amounts of these different adjuvants are those traditionally used in the cosmetic, or dermatological field, and are, for example, from 0.01% to 10% of the total weight of the composition. Those adjuvants, depending on their nature, may be introduced into the fatty phase, into the aqueous phase and/or into lipid spherules.

As oils which can be used in the invention, mineral oils (liquid paraffin), vegetable oils (liquid fraction of shea butter, sunflower oil), animal oils (perhydrosquatene), synthetic oils (Purcellin oil), silicone oils (cyclomethicone) and fluorinated oils (perfluoro polyethers) may be mentioned.

Fatty alcohols, fatty acids (stearic acid) and waxes (paraffin, carnauba, beeswax) may also be used as fatty substances.

As emulsifiers which can be used in the invention, glycerol stearate, polysorbate 60 and the PEG-6/PEG-32/glycol stearate mixture sold under the name Tefose® 63 by the company Gattefosse may be mentioned as examples.

As hydrophilic gelling agents, carboxyvinyl polymers (carbomer), acrylic copolymers such as acrylate/alkylacrylate copolymers, polyacrylamides, polysaccharides such as hydroxypropylcellulose, clays and natural gums may be mentioned, and as lipophilic gelling agents, modified clays such as bentones, metal salts of fatty acids such as aluminum stearates and hydrophobic silica, or alternatively ethylcellulose and polyethylene may be mentioned.

As hydrophilic active agents, proteins or protein hydrolysates, amino acids, polyols, urea, allanloin, sugars and sugar derivatives, water-soluble vitamins, starch and plant extracts, in particular those of Aloe vera may be used.

As lipophilic active agents, retinol (vitamin A) and its derivatives, tocopherol (vitamin E) and its derivatives, essential fatty acids, ceramides and essential oils may be used. These agents add extra moisturizing or skin softening features when utilized.

The compositions of the invention may include other plant or herbal extracts. For example, there may be utilized extracts of Paraguay tea, Kola and Guarana, which provide a source of methylxanthines, saponius, tannins and glycosides that have been shown to reduce swelling and redness. The extract of Paraguay tea is known as "Mate extract" and is described in the "International Cosmetic Ingredient Dictionary", 5th Edition. Mate extract is commercially available in combination with extracts of Kola and Guarana which is sold by Cosmetic Ingredient Resources of Stamford, CT under the trademark "QUENCHT."

Each of mate extract, cromolyn compound and Aloe vera extract are known to provide anti-inflammatory activity. The anti-elastase and anti-tryptase activity of the cromolyn compounds with a corticosteroid when treating minor blemishes has been shown to provide a synergistic effect in treating skin inflammations including sunburn. Soy extract and azelaic acid in combination with the cromolyn compounds are useful for treating hyperpigmentation. About 0.5 to 2% by weight of composition can be utilized although greater amounts would also help in moisturizing.

A surfactant can be included in the composition so as to provide deeper penetration of the ingredients. Although natural surfactants are preferred, others such as isopropyl myristate can be used.

Corticosteroids appear to work synergistically with cromolyn compounds in the treatment of minor irritations or blemishes on humans as well as cats and dogs. Suitable corticosteriods which can be formulated at about 0.25–1% include dexamethasone, bectametasone, betametasone hydrocortisone acetate, hydrocortisone valerate, trimncinoline acetonide, and the like.

The following examples illustrating the compositions of the invention are not intended to limit the scope of the invention. The amounts indicated are by weight percent unless otherwise noted.

EXAMPLE 1

A gel is prepared by admixing the following ingredients.

| Ingredient | Wt % |
| --- | --- |
| Carbomer 940 | 4.10 |
| Xantham gum | 0.15 |
| Propylene glycol | 51.94 |
| Dipropylene glycol | 10.00 |
| Ethoxydiglycol | 15.00 |
| Dimethylisosorbide | 10.00 |
| Aloe vera gel | 8.00 |
| Surfactant | 0.05 |
| Cromolyn sodium | 1.76 |
|  | 100% |

This composition is useful to reduce wrinkles.

EXAMPLE 2

A gel is prepared by admixing the following ingredients:

| Ingredient | Wt % |
|---|---|
| 1. Propylene Glycol | 51.94 |
| 2. Carbomer 940 | 2.10 |
| 3. Dipropylene glycol | 10.00 |
| 4. Xanthan gum | 0.15 |
| 5. Ethoxydiglycol | 15.00 |
| 6. Dimethylisosorbide | 10.00 |
| 7. Ascorbic Acid | 2.00 |
| 8. Chloroxylenol | 0.20 |
| 9. Linoleamidopropyl PG-diammonium chloride phosphate | 1.50 |
| 10. Glycereth 4.5 Lactate | 2.00 |
| 11. Aloe vera gel | 2.00 |
| 12. Cromolyn sodium | 2.00 |
| 13. Tetrasodium EDTA | 0.10 |
| 14. Citric Acid | 0.010 |
| 15. Cocamidopropyl PG-dimonium chloride phosphate | 1.00 |

Ingredients 1 and 2 are mixed to disperse and form a gel. About 80% of ingredient 3 is mixed with ingredient 4, added to the gel and slightly heated with admixture. The balance of 3 is mixed with ingredients 5–10 and added to the gel. Ingredients 11–15 are then admixed and added to the gel at 38 degrees C. After mixing, the gel is brought to room temperature.

This gel composition can be used as an after-sun treatment.

EXAMPLE 3

A lotion is prepared by admixing the following ingredients:

| Ingredient | Wt % |
|---|---|
| Propylene Glycol Stearate | 9.25 |
| Isocetyl alcohol | 5.00 |
| PEG-100 Stearate | 1.20 |
| Water | 69.90 |
| Methyl paraben | 0.20 |
| Propylene glycol | 13.10 |
| Sorbitan palmitate | 0.60 |
| Cromolyn disodium | 6.00 |
| Mate extract | 0.50 |
| Hydrocortisone valerate | 0.25 |
| | 100% |

The lotion can be used to treat itching and hot spots on pets.

EXAMPLE 4

A cream is prepared by admixing the following ingredients:

| Ingredient | Wt % |
|---|---|
| Glycerol stearate | 8.0 |
| PEG-100 stearate | 2.0 |
| Cetostearyl alcohol | 2.5 |
| Disodium EDTA | 0.1 |
| Methyl Paraben | 0.1 |
| Propylene glycol | 6.0 |
| Sorbitan stearate | 0.7 |
| Cromolyn sodium | 2.5 |
| Aloe vera gel | 5.0 |
| Water | 13.5 |
| | 100% |

EXAMPLE 5

An after-sun composition is prepared by admixing the following ingredients:

| Ingredient | Wt % |
|---|---|
| Carbomer | 2.80 |
| Propylene Glycol | 40.05 |
| Disodium EDTA | 1.10 |
| Methyl Paraben | 0.20 |
| Cromolyn sodium | 2.00 |
| Mate extract | 0.35 |
| Aloe vera gel | 52.50 |
| | 100% |

EXAMPLE 6

A solution according to the invention is prepared by admixing the following ingredients:

| Ingredient | Wt % |
|---|---|
| Ethoxyglycol | 15.00 |
| Propylene Glycol | 35.00 |
| Water | q.s. |
| Disodium EDTA | 0.10 |
| Cromolyn sodium | 4.50 |
| Aloe vera gel | 36.75 |
| | 100% |

EXAMPLE 7

A shampoo is prepared by admixing the following ingredients:

| Ingredient | Wt % |
|---|---|
| C12–15 Pareth-7 Carboxylic Acid | 10.0 |
| Isosteoric-6 Carboxylic Acid | 5.0 |
| Hexylene Glycol | 8.0 |
| Chloroxylenol | 0.5 |
| Cromolyn sodium | 2.0 |
| Mate Extract | 0.5 |
| Aloe vera gel | 2.0 |
| Na2 EDTA | 0.1 |
| Water | 71.9 |
| | 100% |

What is claimed is:

1. A method for treating sun-damaged skin, wrinkled skin, chopped lips or chopped skin comprising applying to the skin or lips a cosmetic composition comprising an amount of a cromolyn compound selected from the group consisting of cromolyn, cromolyn sodium and disodium cromolyn effective to treat said sun-damaged skin, wrinkled skin, chopped lips or chopped skin in a suitable cosmetic carrier.

2. The method of claim 1 wherein said composition comprises at least 0.5 percent by weight of said cromolyn compound.

3. The method of claim 2 wherein said composition comprises about 1 to 10% by weight of said cromolyn compounds.

4. The method of claim 1 wherein said composition is in the form of a lotion, cream or gel.

5. The method of claim 1 wherein cromolyn compound is cromolyn sodium.

6. The method of claim 1 wherein cromolyn compound is disodium cromolyn.

7. The method of claim 1 wherein said carrier comprises Aloe vera.

* * * * *